United States Patent [19]
Vo-Dinh et al.

[11] Patent Number: 5,579,773
[45] Date of Patent: Dec. 3, 1996

[54] LASER-INDUCED DIFFERENTIAL NORMALIZED FLUORESCENCE METHOD FOR CANCER DIAGNOSIS

[75] Inventors: Tuan Vo-Dinh; Masoud Panjehpour; Bergein F. Overholt, all of Knoxville, Tenn.

[73] Assignee: Martin Marietta Energy Systems, Inc., Oak Ridge, Tenn.

[21] Appl. No.: 316,132

[22] Filed: Sep. 30, 1994

[51] Int. Cl.$^6$ ...................................... A61B 6/00
[52] U.S. Cl. ........................................... 128/665
[58] Field of Search .................... 128/633, 634, 128/630, 665, 897, 898; 607/89, 901; 250/461.2; 356/318

[56] References Cited

U.S. PATENT DOCUMENTS

| | | |
|---|---|---|
| 4,479,499 | 10/1984 | Alfano ..................................... 128/665 |
| 4,675,529 | 6/1987 | Kushida .................................. 128/634 |
| 4,718,417 | 1/1988 | Kittrell et al. ............................ 606/15 |
| 4,930,516 | 6/1990 | Alfano et al. . |
| 4,957,114 | 9/1990 | Zeng et al. .............................. 128/665 |
| 4,981,138 | 1/1991 | Deckelbaum et al. ................... 128/665 |
| 5,003,977 | 4/1991 | Suzuki et al. ........................... 128/633 |
| 5,042,494 | 8/1991 | Alfano et al. . |
| 5,115,137 | 5/1992 | Andersson-Ergels et al. ......... 128/633 |
| 5,131,398 | 7/1992 | Alfano et al. . |
| 5,261,410 | 11/1993 | Alfano et al. . |
| 5,303,026 | 4/1994 | Strobl et al. . |
| 5,315,993 | 5/1994 | Alcala .................................. 250/461.2 |
| 5,348,018 | 9/1994 | Alfano et al. .......................... 128/633 |
| 5,421,337 | 1/1995 | Richards-Kortum et al. .......... 128/665 |
| 5,421,339 | 6/1995 | Ramanujam et al. .................. 128/665 |

Primary Examiner—Angela D. Sykes
Assistant Examiner—Eric F. Winakur
Attorney, Agent, or Firm—E. A. Pennington; H. W. Adams

[57] ABSTRACT

An apparatus and method for cancer diagnosis are disclosed. The diagnostic method includes the steps of irradiating a tissue sample with monochromatic excitation light, producing a laser-induced fluorescence spectrum from emission radiation generated by interaction of the excitation light with the tissue sample, and dividing the intensity at each wavelength of the laser-induced fluorescence spectrum by the integrated area under the laser-induced fluorescence spectrum to produce a normalized spectrum. A mathematical difference between the normalized spectrum and an average value of a reference set of normalized spectra which correspond to normal tissues is calculated, which provides for amplifying small changes in weak signals from malignant tissues for improved analysis. The calculated differential normalized spectrum is correlated to a specific condition of a tissue sample.

14 Claims, 5 Drawing Sheets

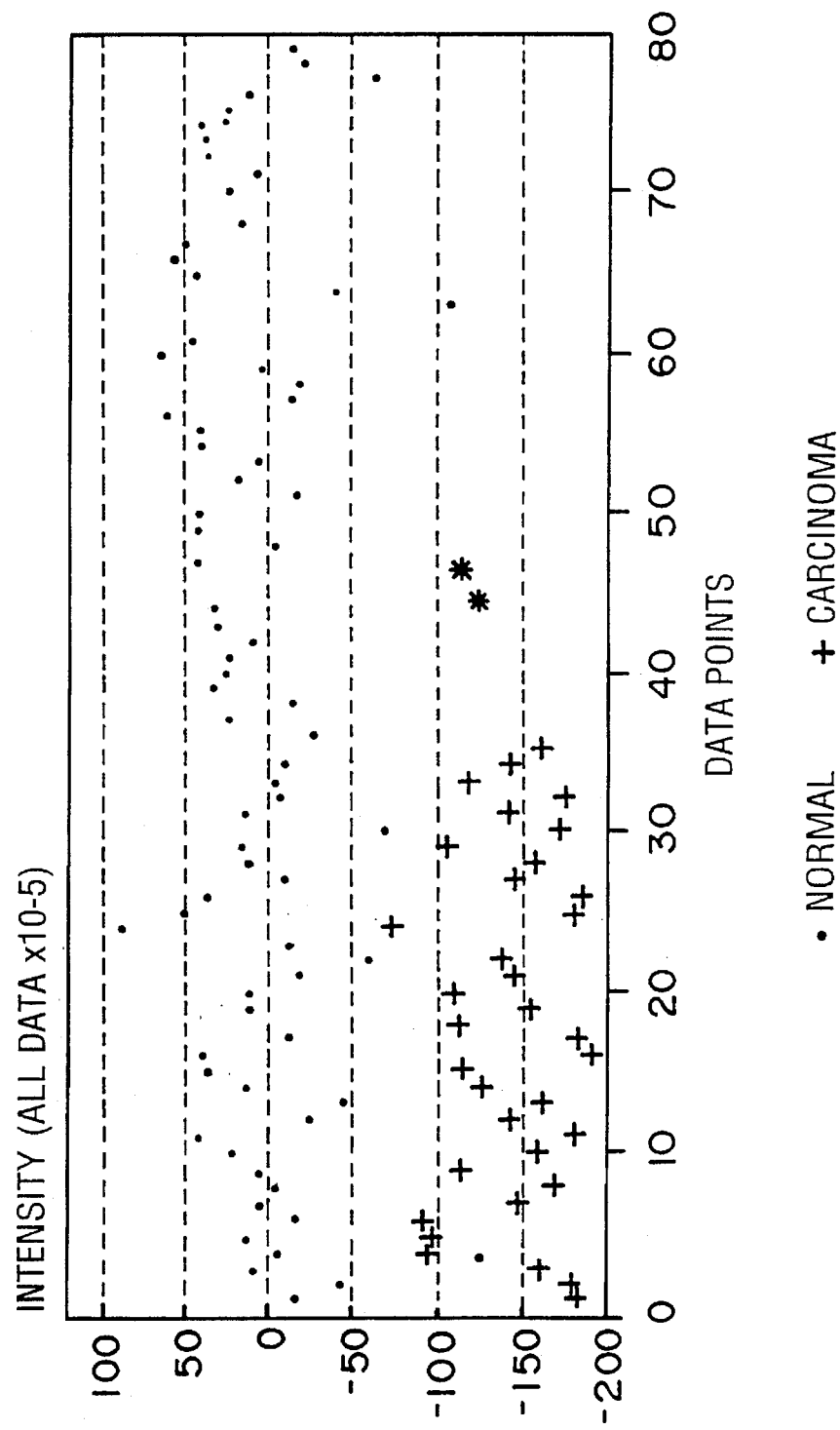

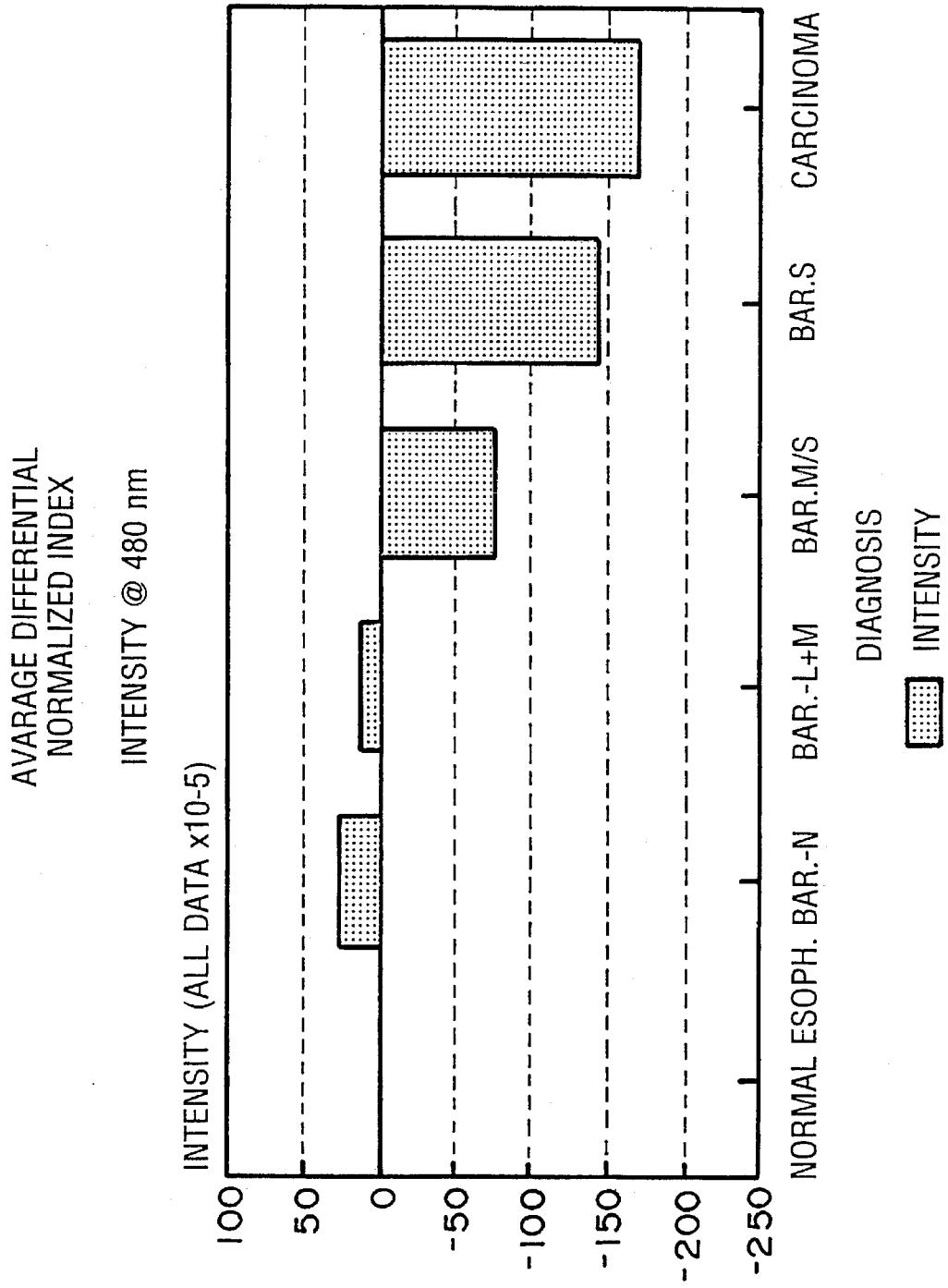

LASER-INDUCED DIFFERENTIAL NORMALIZED FLUORESCENCE METHOD FOR CANCER DIAGNOSIS

This invention was made with Government support under contract DE-AC05-840R21400 awarded by the U.S. Department of Energy to Martin Marietta Energy Systems, Inc. and the Government has certain rights in this invention.

FIELD OF THE INVENTION

The present invention relates generally to the field of medical diagnostics and, more specifically, to an improved in vivo method for making a cancer diagnosis using differential normalized fluorescence (DNF). A sample is irradiated with a laser light source and the laser-induced fluorescence (LIF) of normal and malignant tissues are normalized by dividing the intensity at each wavelength by the integrated area under the spectrum. Differences in the resulting DNF curves are then used as the basis for cancer diagnosis.

BACKGROUND OF THE INVENTION

In vivo and rapid procedures for tissue diagnosis are important for efficient cancer detection and therapy. As an example of one type of detection, endoscopy is used to detect abnormal tissues in the human esophagus. Once an abnormality is found, biopsies are taken for determination of histopathology.

For diagnosis, a biopsy sample usually represents a very small area. The laboratory results are generally not available for several days. Thus, the known endoscopic techniques do not provide real-time in vivo classification of the tissue type.

Recently there has been interest in using laser-induced fluorescence (LIF) in the development of diagnostic and therapeutic tools. A number of investigators have used LIF as a method to discriminate tumors from normal tissues. For example, The LIF technique has been used to distinguish adenomatous polyps from normal colon tissue and hyperplastic polyps in vitro. See C. R. Kapadia et al., "Laser-Induced Fluorescence Spectroscopy of Human Colonic Mucosa—Detection of Adenomatous Transformation," *Gastroenterology*, 99: 150–157 (1990).

Still others have investigated the LIF technique to distinguish adenomatous tissue from normal colon tissue in vivo. See R. M. Cothren et al., Gastrointestinal Tissue Diagnosis By Laser-Induced Fluorescence Spectroscopy at Endoscopy," *Gastrointestinal Endoscopy*, 36: 105–111, (1990). Fluorescence techniques have also been used to characterize normal and malignant breast tissues, lung tissues, and to quantify photodynamic therapy drugs in rat tissues. A fiber optic LIF antibody-based biosensor has been used to detect DNA modification by carcinogenic chemicals in human placenta samples.

Other investigators have used LIF and multivariate linear regression analysis to distinguish neoplastic tissue from non-neoplastic tissue. See K. T. Schomacker et al., Ultraviolet Laser-Induced Fluorescence of Colonic Tissue: Basic Biology and Diagnostic Potential," *Lasers In Surgery and Medicine*, 12: 63–68 (1992).

The Schomacker et al. data suggest that the LIF measurements detected changes in polyp morphology rather than changes in fluorosphores specific to polyps, and it was this change in morphology that leads indirectly to discrimination of polyps. Schomacker et al. concluded that the feasibility of discriminating groups of normal from dysplastic cells by LIF is as yet undemonstrated.

U.S. Pat. No. 4,930,516 to Alfano et al. describes a method for detecting cancerous tissue using laser-induced fluorescence. The wavelengths at which maximum intensities are attained for sample tissue are determined and compared to peak wavelengths derived from known non-cancerous tissue.

U.S. Pat. No. 5,131,398 to Alfano et al. describes a method of distinguishing cancerous tissue from benign tumor tissue using a light source which produces a 300-nm monochromatic light beam which is directed into the sample through an endoscope. Emission radiation produced by fluorescence is measured at 340 and 440 nm, and a ratio of the two intensities is then calculated and used as a basis for determining if the tissue is cancerous.

A further endoscopic technique is described in U.S. Pat. No. 5,261,410 to Alfano et al. uses an infrared monochromatic light source, and then measures the Raman shift in emission radiation to ascertain the condition of a tissue sample.

The foregoing references and studies detailed therein indicate that there remains a strong need to develop improved procedures for effective cancer diagnosis.

SUMMARY OF THE INVENTION

An object of the present invention is to provide a method of performing in vivo cancer diagnosis without requiring biopsy.

Another object of the present invention is to provide a method of performing an in vivo medical diagnosis in which the results can be obtained quickly and reliably.

Yet another object of the present invention is to provide a method and apparatus of performing an in vivo medical diagnosis using laser-induced fluorescence wherein the spectral changes are less dependent on spectral intensity and thus more reliably indicative of a tissue condition.

Still another object of the present invention is to provide a method and apparatus wherein small changes in weak signals from malignant tissues are amplified by the differential normalization procedure for improved analysis.

These and other objects of the invention are met by providing a method of performing a medical diagnosis which includes the steps of irradiating a tissue sample with a monochromatic excitation light having a predetermined wavelength, producing a laser-induced fluorescence spectrum from emission radiation generated by interaction of the excitation light with the tissue sample, dividing the intensity at each wavelength of the spectrum by the integrated area under the spectrum to produce a normalized spectrum, and correlating the normalized spectrum to a specific condition of the tissue sample.

An apparatus for performing the diagnostic method includes a laser source producing a beam at 410 nm for detection of cancer of the esophagus.

Other objects, advantages and salient features of the invention will become apparent from the following detailed description, which taken in conjunction with the annexed drawings, discloses preferred embodiments of the invention.

BRIEF DESCRIPTION OF THE DRAWINGS

FIG. 4 is a graph showing a differential normalized index at 480 nm, with results of histopathology assays marked on the graph for normal tissues and malignant tissues; and FIG. 5 is a graph showing average differential normalized fluorescence values at 480 nm for various tissues.

DETAILED DESCRIPTION OF THE INVENTION

Figure 1:
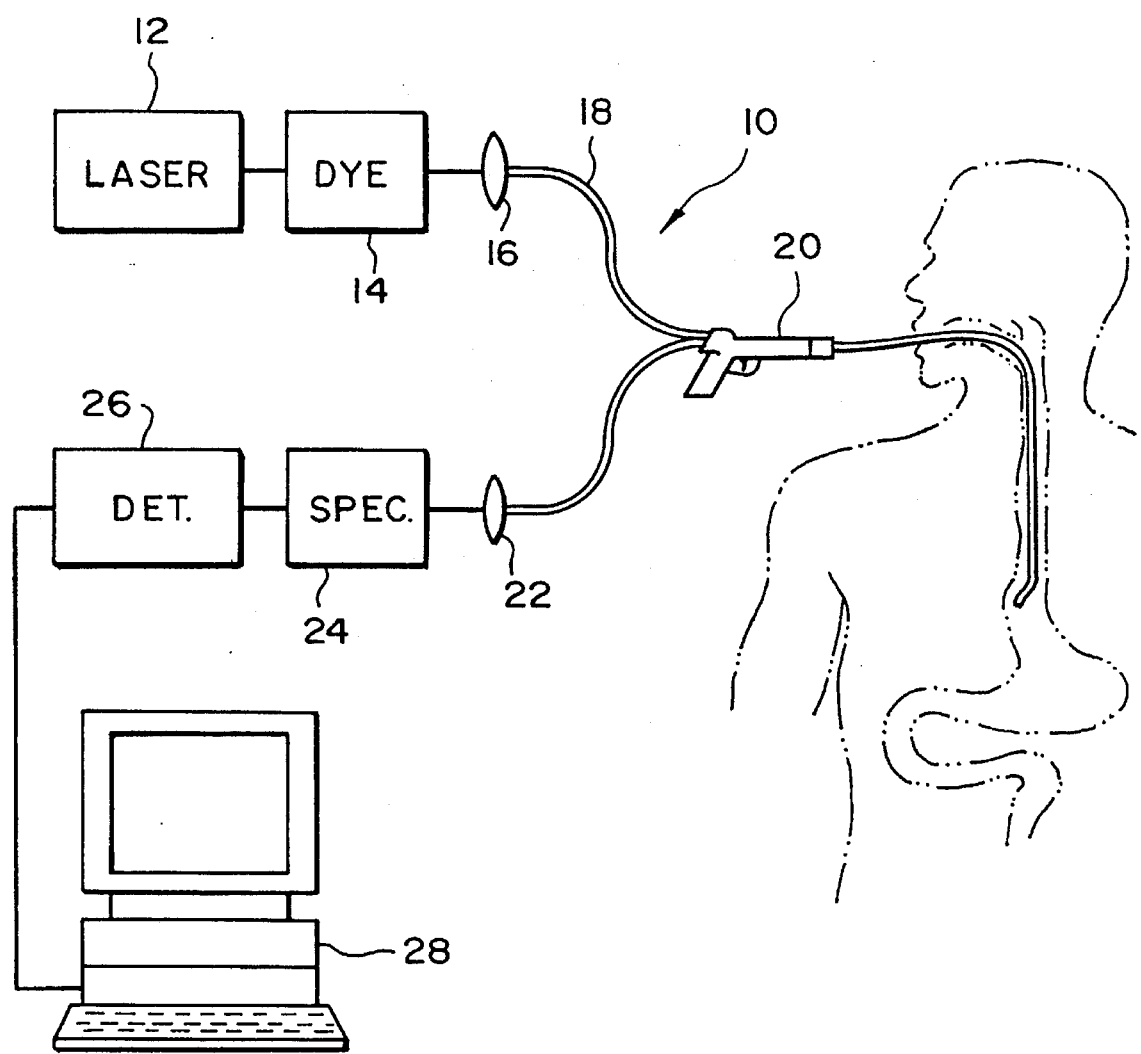
FIG. 1 is a schematic view of an apparatus for conducting a differential normalized fluorescence diagnostic method of the present invention.

Referring to FIG. 1, an instrument 10 for conducting cancer diagnosis in vivo can be set up in an operating room of a hospital or other suitable examination room. A source 12 of monochromatic excitation light produces a pulsed beam which is tuned to a specific wavelength by a dye head (DYE) 14. Preferably, for detecting and differentiating normal and malignant tumors of the esophagus, the source 12 is a pulsed nitrogen-pumped dye laser (model LN300C Laser Photonics, Inc., Orlando, Fla. USA) tuned to 410 nm.

The pulsed output beam passes through a focusing lens 16 and into a bifurcated optical fiber bundle 18. The bundle 18 includes, for example, seven 200-µm diameter fibers for excitation and twelve 200-µm diameter fibers for emission. The bundle is designed so that it can be inserted into the biopsy channel of an endoscope 20. The distal end of the bundle is juxtaposed to the tissue in vivo for analysis, and preferably touching the tissue (although not necessarily).

Emission radiation in the form of laser-induced fluorescence is delivered through the bundle 18 to a focusing lens 22, which is optional, and then to a sensor means. The sensor means may include a spectrograph (SPEC.) 24 and multichannel detector (DET.) 26. In a preferred embodiment, the detector 26 is an intensified photodiode array (model OMA III, EG&G Princeton Applied Research, Princeton, N.J. USA) equipped with a spectrograph (model 1235 EG&G) for spectral dispersion. Alternatively, a polychromator or other light detectors may be used.

The output signal from the light detector is delivered to a computer 28 which is supplied with commercially available data acquisition software.

In an alternate embodiment the detector can be a gated multichannel detector operated in a time-resolved mode with a delay time optimized to the lifetime of fluorescent components of interest in tissues. Selection of appropriate gate and delay times can further enhance spectral features.

Yet in another alternate embodiment, the excitation laser intensity can be modulated and the detector synchronized in a phase-resolved mode to improve detection, sensitivity, and selectivity.

Procedures for Clinical Measurements

All measurements were conducted during routine gastrointestinal endoscopy examinations of patients. The fiber optic probe was inserted into the biopsy channel of the endoscope. The distal end of the fluorescence probe is positioned to lightly touch the surface of the tissue being monitored. Each LIF reading corresponded to fluorescence measurements for ten excitation pulses. The system is programmed to take the fluorescence for each laser pulse. Background reading is subtracted from the accumulated data and the resulting spectra are stored in a special data file. A minimum of three readings are recorded for each tissue site. A small light source located close to the endoscopic monitor sends flashes for every laser pulse delivered to the tissue. These flashes allow the endoscopist to visually determine the exact site of analysis and to ensure proper contact of the probe to the tissue during fluorescence measurements. The reading is completed in approximately 0.6 seconds for each tissue site.

In general, the LIF spectra of normal and malignant tissues exhibit certain differences at several wavelengths. However, it is difficult to observe subtle but consistent differences in the raw data because these differences are often masked by large variations in intensity.

Figure 2:
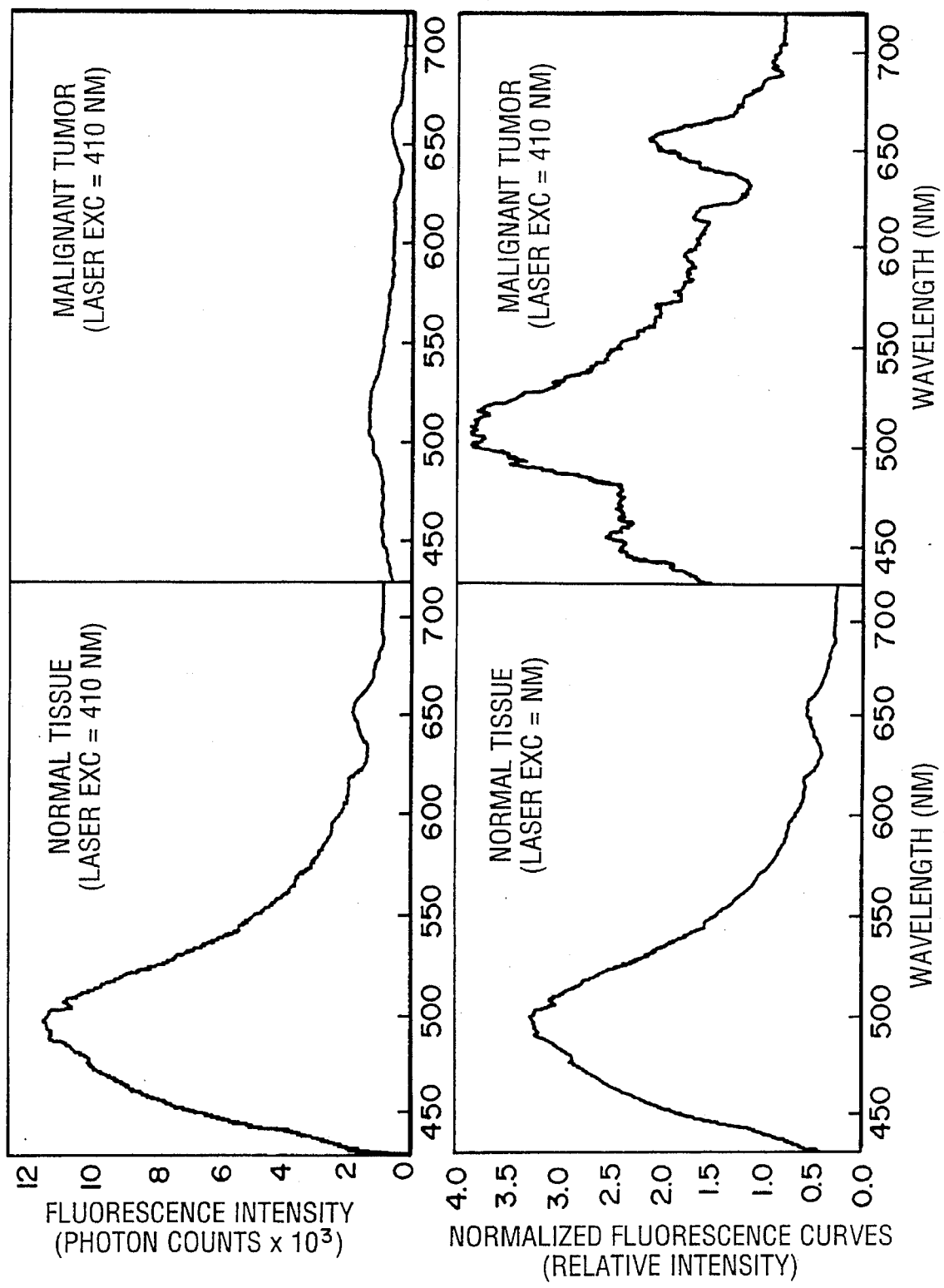
FIG. 2 presents graphs showing fluorescence emission of normal and malignant tissue using non-normalized and normalized data, respectively.

An example of fluorescence emission of a normal tissue and a malignant tissue is illustrated in FIG. 2(a). The laser excitation wavelength was selected to be 410 nm. To develop an effective technique capable of differentiating normal and malignant tissues, it is essential to investigate and select the optimal experimental conditions and parameters affecting the results of LIF measurements. The first such parameter is the laser excitation wavelength. With a nitrogen laser, the lowest excitation wavelength (highest energy) available is 337 nm. Longer wavelengths could be selected for excitation by using the tunable dye system 14 of FIG. 1.

In general, the use of shorter wavelengths would excite more components, whereas the use of longer wavelengths would excite less components in tissues. The choice of the laser excitation wavelength is important since, with a fixed excitation laser, it is not possible to excite all tissue components in a single measurement. One approach is to excite as many tissue components as possible at the wavelengths where they exhibit the strongest absorption. This approach, however, does not necessarily produce the best results since certain important but subtle spectral changes could be masked by strong but non-specific absorption bands. After performing a number of experiments, the 410-nm laser wavelength was selected for certain cancers. This wavelength produces fluorescence spectra having certain specific spectral features that are useful to the development of the present diagnostic methodology.

The data in FIG. 2(a) show that the fluorescence intensity of the malignant tissue (right curve) is much weaker than that of the normal tissue (left curve). However, this general observation based on the intensity is often difficult to be used in practice because the intensity of the recorded fluorescence signals are not always a consistent parameter as it depends on many factors including blood flow, hemoglobin absorption, tissue surface morphology, distance between the tissue surface and the probe, etc. For comparison purposes, the two spectra in FIG. 2(a) are plotted on the same intensity scale. It is noteworthy that the detection of small spectral structures in the weak fluorescence signal from the malignant tumor (FIG. 2(a), right curve) are generally difficult.

Whereas the intensity of the fluorescence is not always a consistent parameter, the present invention takes into account that the spectral profile of each spectrum contained specific characteristics that are more consistent. Based on this observation, the present invention uses the differential normalized fluorescence (DNF) to enhance small but consistent spectral differences between the normal and malignant tissues.

In order to amplify and compare the spectral features in fluorescence spectra of normal and malignant tissues, the present invention uses a normalization process that divides the intensity at each wavelength by the integrated area under the total spectrum. The normalized fluorescence intensity $I_n$ at wavelength i for sample K, i.e., $I_n(K)$ i, is given by:

$$I_n(K)_i = I(K)_i / \Sigma_i I(K)_i$$

where $I(K)_i$ is the fluorescence at wavelength i for sample K, and $\Sigma_i$ corresponds to the summation of fluorescence intensities at all wavelengths i over the spectral range investigated.

FIG. 2(b) illustrates the effect of this procedure for the same normal esophageal tissue (left curve) and the same malignant esophageal tissue (right curve). This procedure is designed to produce two important effects on the fluorescence data. First, it produces a "normalization" effect. Since each spectrum is normalized with respect to the integrated intensity of the entire spectrum, the resulting spectrum becomes less dependent on the intensity factor.

It is noteworthy that the normalized intensity $In_i$ has a dimensionless value since it is the ratio of an intensity (dimension in photons) divided by a sum of intensities $\Sigma_i I(K)_i$, (which also has a dimension in photons).

Another important effect of this normalization procedure is the enhancement of small spectral features in weak fluorescence signals. This unique effect of the DNF method is essential for the diagnosis of malignant tissues, which generally exhibit weak fluorescence whose small features are difficult to detect. As the result of this normalization procedure, the differences in spectral features between the normalized fluorescence spectra of normal and malignant tissues becomes more easily detected (see FIG. 2(b) section: compare left and right curve).

As shown in FIG. 2(b), the two noticeable features were the spectral features at 460–490 nm and 640–670 nm. A depleted area at approximately 475–480 nm can be observed in the spectra of malignant tissues. This spectral depletion reflected deficiency of certain components (or absorption by some compound) in malignant tissues, which normally fluoresce at 460–490 nm. This spectral deficiency (i.e., "negative peak") provides an important criterion for malignant tissue diagnosis. To our knowledge, this important spectral feature has not been reported in any previous studies.

Another important feature in the normalized fluorescence spectra is that several bands between 640 and 670 nm in the fluorescence spectra of malignant tumors are relatively more intense than those of normal tissues. In addition there are also minor spectral features noticeable in the normalized curve of malignant tissues (FIG. 2(b)) at 590 and 625 nm.

Using the normalized spectra, we have developed a DNF technique designed at exploiting these spectral differences between normal and malignant tissues. Noticing that the normalized fluorescence spectra of all normal tissues have similar spectral profile, we established a "baseline curve" for normal tissues. This baseline curve was determined as the mean average of normalized fluorescence spectra from a reference set of normal tissue samples. The intensity of this baseline curve, $I_B$, at wavelength i is given by:

$$I_{Bi} = \left( \frac{1}{n_B} \right) \times \Sigma_B I(B)_i \quad (2)$$

where $\Sigma_B$ corresponds to a normal tissue B used in the baseline set.

It is noteworthy that this procedure requires the identification of a set of normal tissues (and patients) a priori in order to establish the baseline curve. The data necessary for the baseline curve can be initially based on histopathology assay data. Once the baseline curve is established, it can be used for all future measurements, and the fluorescence characteristics of each tissue can be compared to this baseline curve.

After the establishment of the baseline fluorescence curve, the DNF curve for a specific tissue sample of interest was calculated as the difference between its normalized fluorescence spectrum $I_n$ and the baseline curve $I_B$. This procedure involved subtracting the intensity of the baseline curve from the normalized intensity curve of the sample of interest. The DNF Intensity of particular tissue sample K at wavelength i is given by:

$$I_{DNF}(K)_i = I_n(K)_i - I_B \quad (3)$$

Figure 3:
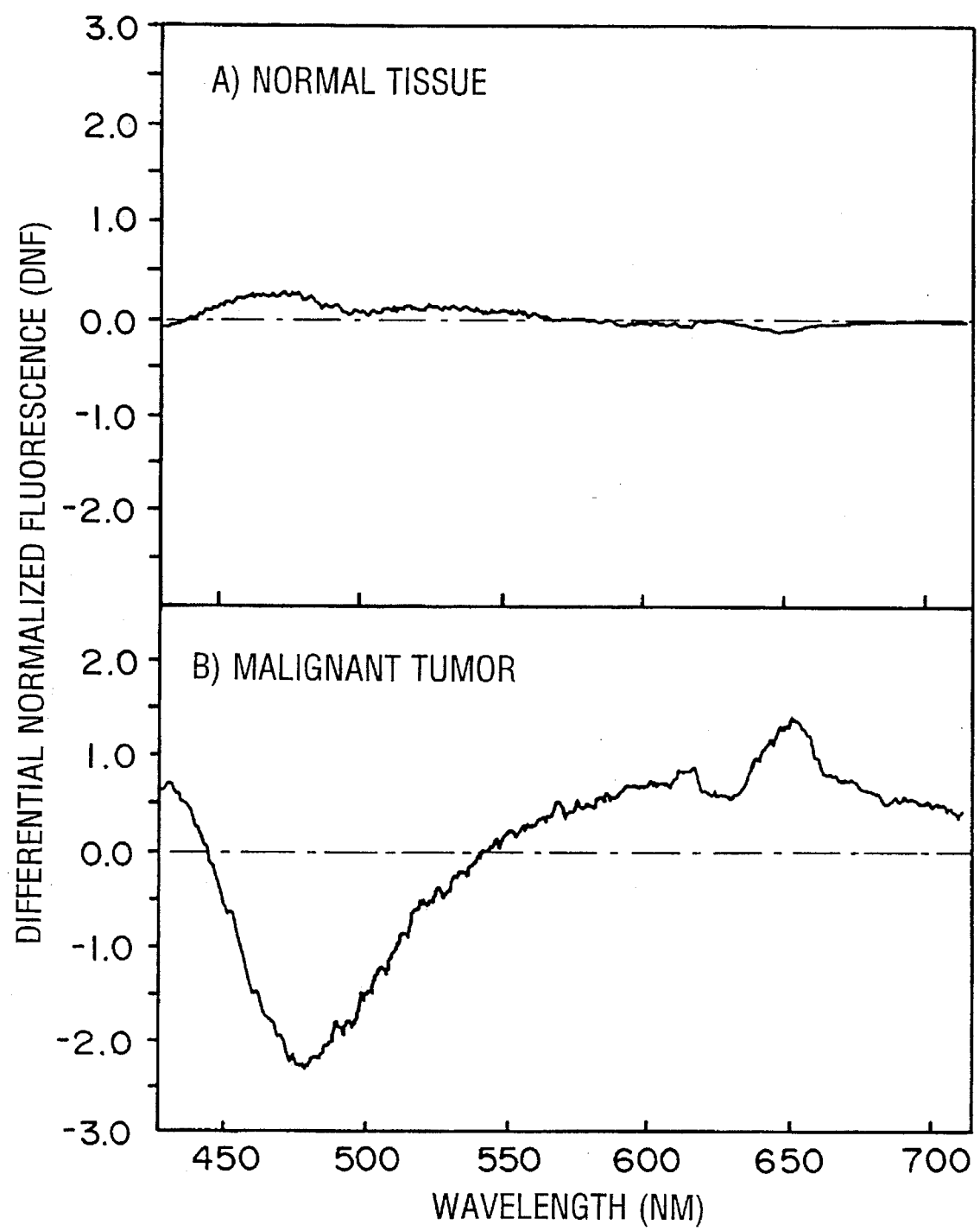
FIG. 3 is a graph showing (a) DNF of a normal esophageal mucosa and (b) DNF of an esophageal adenocarcinoma, with curve (b) showing a negative peak at 475–480 nm which is characteristic of malignant tissue in the esophagus.

The DNF spectrum, i.e., the plot of intensity $I_{DNF}(k)_i$ versus wavelength i, is illustrated in FIG. 3. This figure shows the DNF curves corresponding to a normal tissue and a malignant tumor in sections A and B, respectively, after subtraction of the baseline curve $I_{Bi}$ as described in Equation 3. As expected, the DNF curve that corresponds to a normal tissue is a line close to the horizontal baseline, since there is little difference between the normalized fluorescence spectrum of a given normal tissue and the mean average of a reference set of normal tissues, $I_{Bi}$. On the other hand, one expects to observe some differences between the normalized fluorescence of a malignant tumor and $I_{Bi}$. The results of the DNF procedure confirmed this important feature and clearly showed a negative peak at 475–480 nm for malignant tissues as illustrated in FIG. 3.

The $I_{DNF}$ values at 480 nm are shown in FIG. 4 for a set of samples from a data base of 300 measurements with over 80 patients. Biopsies of normal and malignant tissue samples from patients investigated by laser-induced fluorescence were also analyzed histopathologically with results shown in FIG. 4. The normal tissues labeled by a dot (.), and malignant tissues labeled by a cross (+). The results show that all 35 malignant tumors have a negative DNF-1 index with a value less than $-7.5 \times 10^{-4}$, which corresponds to the negative peak in malignant tissue fluorescence discussed previously in FIG. 2. On the other hand, the values of the DNF-1 index of all 79 normal tissues, except for one sample, are distributed around zero (between $-5 \times 10^{-4}$ and $5 \times 10^{-4}$) as expected since they come from the difference between the normalized fluorescence curve of a normal tissue and the baseline curve of a set of normal tissues.

Classification of Carcinoma and Normal Tissues

In a study using the methodology of the present invention, data related to the first 30 patients were made available to the investigators in order to compare with fluorescence data, to calculate the baseline curve, and to develop the DNF model. After this initial phase, all the measurements were "blind tests" and the DNF model was used to "predict" the diagnosis of tissues for all other patients. For this blind test phase, histopathology test results were unknown a priori by the investigators.

As shown in FIG. 4, classification of malignant tissues using the DNF-1 indices is in excellent agreement with histopathological results for the set of patients monitored in this study. In the data set shown in FIG. 4, all 35 malignant tissues detected by the DNF method are in excellent agreement with biopsy results. From 77 normal tissues classified as normal by the DNF method, only one was found to be malignant by histopathological assays. Although the exact causes of this misclassification is not completely understood, a possibility might be due to the fact that the area monitored by the optical technique was not exactly the same location where the biopsy was made. Other DNF readings in this patent classified correctly.

Two interesting cases are shown in FIG. 4 by two stars (*). These two samples, which are related to the same patient, were first diagnosed to be normal tissues by the conventional biopsy procedure. However, the laser-based DNF method classified these samples to be malignant. The decision was made to rediagnose this patient using an independent procedure (viz., CAT scan method). The computer assisted tomography (CAT) scan measurements revealed that this patient had lung cancer that had spread into areas underlining the esophagus mucosa. This example underscores the effectiveness of the optical DNF technique to diagnose malignant tissues that could have been misdiagnosed by the conventional biopsy method.

It is noteworthy that this study uses the normal (i.e., 0th order) normalized spectra (FIGS. 2b) and 0th order DNF curves (FIG. 3). In certain cases, small spectral features in the curves can be further enhanced by using first-derivative, second-derivative or $n^{th}$ derivative curves.

Analysis of Barrett's Esophagus

In addition to normal and malignant tissues, there is a type of dysplasia, called Barrett's esophagus, which is difficult to detect by conventional endoscopy. FIG. 5 shows the average values of the DNF index at 480 nm corresponding to various types of tissues: normal esophagus, normal Barrett's mucosa (BAR.N), low-to-moderate dysplasia (BAR.LM), moderate-to-severe dysplasia (BAR.MS), severe dysplasia (BAR.S), and carcinoma.

In order to discuss the results in FIG. 5, it is useful to understand the nature of Barrett's tissues. Barrett's esophagus, a progressive columnar metaplasia of the lower esophagus, is a premalignant condition with an increased risk of adenocarcinoma. In this work the diagnostic procedure for Barrett's esophagus is different from that of carcinoma normal tissues. Carcinoma tissues are often clear-cut cases that can be visually seen by the physician through his or her endoscope. Therefore, it was possible to perform an optical LIF measurement on a specific area and later perform a biopsy on the same location. With this procedure, it is possible to have a precise (one-to-one) comparison between the two methods for one type of tissue. Barrett's tissues do not often correspond to visually clear-cut cases. In Barrett's esophagus, the original squamous epithelial cell lining of the esophagus is replaced by a metaplastic columnar-type epithelium, often given rise to a mixture of tissue islands of columnar epithelium with diffuse boundaries.

In testing the present techniques, rapid performance of LIF measurements occurred first, and then biopsies were taken in the same areas. Approximately 5–7 LIF measurements in different locations can be taken in the same time required for one regular biopsy. Although great care was taken to perform the biopsies in the areas previously measured by LIF, it is often difficult to find the exact locations of the Barrett's tissues that had been previously analyzed by LIF. Therefore, for Barrett's esophagus tissues, it is not possible to have a precise and exact comparison between the optical DNF results and the biopsy data.

The data related to Barrett's esophagus is presented with the average DNF values of the Barrett's tissues grouped in the different classifications used by the pathologist, i.e., BAR.N, BAR.M-L, BAR.M-S, BAR. S.

The results in FIG. 5 indicate that the DNF index at 480 nm show an interesting general trend: the more severe the Barrett's dysplasia, the more negative the average DNF index value. For example, tissues designated as Barrett's normal and Barrett's low-to-medium have DNF values close to zero (i.e., similar to normal tissues). Tissues designated by the pathologist as Barrett's medium-to severe have an average DNF value approximately $7.5 \times 10^{-4}$ whereas Barrett's severe tissues have DNF values at approximately $15 \times 10^{-4}$. Carcinoma tissues have an average DNF value at approximately $17 \times 10^{-4}$. It is noteworthy that these results provide a general trend which could be used to improve the diagnosis of dysplasia in Barrett's esophagus. Improved procedures to diagnose Barrett's dysplasia in esophagus are currently under investigation in our laboratories.

The present invention provides a unique technique that can provide effective indices to diagnose malignant tumors in the esophagus. The DNF indices, which are derived from in-vivo laser-induced fluorescence measurements, have provided excellent results in the diagnosis of malignant tumors of the esophagus. From the total of 114 samples studied, there is only one case where the DNF result differs from the biopsy data. There are two samples in which the DNF method reveals malignance in tissues that were missed by the biopsy method.

The DNF procedure also provides a general trend which corresponds to severity of dysplasia for Barrett's esophagus. Thus, using the present DNF method, one can provide a rapid in vivo technique for cancer diagnosis which does not require biopsy, thus decreasing the time and cost of cancer prevention and treatment.

While advantageous embodiments have been chosen to illustrate the invention, it will be understood by those skilled in the art that various changes and modifications can be made therein without departing from the scope of the invention as defined in the appended claims.

What is claimed is:

1. An apparatus for performing a medical diagnosis comprising:

means for radiating a tissue sample with a monochromatic excitation light having a predetermined wavelength;

means for producing a laser-induced fluorescence spectrum, having a plurality of wavelengths with an intensity at each of the plurality of wavelengths, from emission radiation generated by interaction of the excitation light with the tissue sample;

means for calculating an area under the laser-induced fluorescence spectrum to generate an integrated area;

means for dividing the intensity at each wavelength of the laser-induced fluorescence spectrum by the integrated area under the laser-induced fluorescence spectrum to produce a normalized spectrum; and means for correlating the normalized spectrum to a specific condition of the tissue sample.

2. An apparatus according to claim 1, wherein the radiating means comprises a laser having a wavelength of about 410 nm.

3. An apparatus according to claim 2, wherein the radiating means further comprises an endoscope and a fiber optic bundle for directing excitation light into the endoscope and detecting emission radiation from the tissue through another fiber optic bundle.

4. An apparatus according to claim 2, wherein the correlating means include means for analyzing the normalized spectrum at about 480-nm.

5. An apparatus according to claim 2, wherein the correlating means include means for analyzing the normalized spectrum at around 660-nm.

6. An apparatus according to claim 1, wherein the radiating means comprises a pulsed laser and the correlating means is a gated photodetector used in a time-resolved mode.

7. An apparatus according to claim 1, wherein the radiating means comprises a pulsed laser having a wavelength of about 410-nm, and the correlating means is a gated photodetector used in a time-resolved mode.

8. An apparatus according to claim 1, wherein the radiating means comprises a modulated laser and the correlating means comprises a synchronized photodetector operated in a phase-resolved mode.

9. An apparatus according to claim 1, wherein the radiating means comprises a laser producing an amplitude-modulated light at about 410-nm, and the correlating means comprises a synchronized detector operated in a phase-resolved mode.

10. An apparatus according to claim 1, wherein the means for producing a laser induced fluorescence spectra includes a multichannel detector including an array of photodiodes.

11. A method of performing a medical diagnosis comprising the steps of:

exposing a tissue sample to a monochromatic excitation light having a predetermined wavelength;

detecting emission radiation from the tissue sample generated in response to the monochromatic excitation light;

producing a laser-induced fluorescence spectrum from the emission radiation, the laser-induced fluorescence spectrum having a plurality of wavelengths with an intensity at each of the plurality of wavelengths;

integrating an area under the laser-induced fluorescence spectrum to produce an integrated area;

dividing the intensity at each of the plurality of wavelengths of the laser-induced fluorescence spectrum by the integrated area to produce a normalized spectrum;

calculating a mathematical difference between the normalized fluorescence spectrum and an average value of a reference set of normalized spectra which correspond to normal tissues;

producing a differential normalized fluorescence spectrum from the mathematical difference; and correlating the differential normalized fluorescence spectrum to a specific condition of the tissue sample.

12. A method according to claim 11, wherein the step of exposing includes exposing a tissue sample to monochromatic excitation light having a wavelength of about 410 nm.

13. A method according to claim 11, wherein the correlating step comprises determining a wavelength at which normal tissue fluoresces, and identifying a depletion in the intensity at the wavelength at which normal tissue fluoresces.

14. A method according to claim 11, wherein the correlating step comprises calculating a derivative curve of the differential normalized fluorescence spectrum.

* * * * *